(12) United States Patent
Lee et al.

(10) Patent No.: US 8,026,369 B2
(45) Date of Patent: Sep. 27, 2011

(54) COMPOSITION CONTAINING THIAZOLE RINGS, ORGANIC SEMICONDUCTOR POLYMER CONTAINING THE COMPOSITION, ORGANIC ACTIVE LAYER CONTAINING THE ORGANIC SEMICONDUCTOR POLYMER, ORGANIC THIN FILM TRANSISTOR CONTAINING THE ORGANIC ACTIVE LAYER, ELECTRONIC DEVICE CONTAINING THE ORGANIC THIN FILM TRANSISTOR AND METHOD OF PREPARING THE SAME

(75) Inventors: Bang Lin Lee, Suwon-si (KR); Eun Kyung Lee, Seoul (KR); Joo Young Kim, Suwon-si (KR); Kook Min Han, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 732 days.

(21) Appl. No.: 12/007,307

(22) Filed: Jan. 9, 2008

(65) Prior Publication Data
US 2008/0191201 A1 Aug. 14, 2008

(30) Foreign Application Priority Data
Jan. 24, 2007 (KR) .................. 10-2007-0007500

(51) Int. Cl.
*C07D 277/20* (2006.01)
*H01L 51/30* (2006.01)
(52) U.S. Cl. .... 548/146; 548/202; 257/40; 257/E51.029
(58) Field of Classification Search .................. 548/146, 548/202–203, 205; 257/40, E51.001, E51.024–E51.025, E51.029
See application file for complete search history.

(56) References Cited

U.S. PATENT DOCUMENTS

| 5,625,199 | A | 4/1997 | Baumbach et al. |
| 5,946,551 | A | 8/1999 | Dimitrakopoulos et al. |
| 6,107,117 | A | 8/2000 | Bao et al. |
| 6,166,172 | A | 12/2000 | McCullough et al. |

(Continued)

FOREIGN PATENT DOCUMENTS
JP 2006-241359 9/2006
(Continued)

OTHER PUBLICATIONS

Kojima, T., et al. "High-Performance n-Type Organic Field-Effect Transistors Based on Co-Oligomers Containing a Trifluoromethylphenylthiazolyl Group and a Biphenylene Core." Chem. Lett., vol. 36 (2007): pp. 1198-1199 and Supplemental.*

(Continued)

*Primary Examiner* — Matthew W Such
(74) *Attorney, Agent, or Firm* — Harness, Dickey & Pierce, P.L.C.

(57) ABSTRACT

Disclosed herein is a composition containing hetero arylene or arylene showing a p-type semiconductor property in addition to thiophene showing a p-type semiconductor property and thiazole rings showing a n-type semiconductor property at a polymer main chain, an organic semiconductor polymer containing the composition, an organic active layer containing the organic semiconductor polymer, an organic thin film transistor (OTFT) containing the organic active layer, an electronic device containing the OTFT, and a method of preparing the same. The composition of example embodiments, which is used in an organic semiconductor polymer and contains thiazole rings, may exhibit increased solubility to an organic solvent, coplanarity, processibility and an improved thin film property.

4 Claims, 2 Drawing Sheets

U.S. PATENT DOCUMENTS

| | | | |
|---|---|---|---|
| 6,232,157 | B1 | 5/2001 | Dodabalapur et al. |
| 6,452,207 | B1 | 9/2002 | Bao |
| 7,030,409 | B2 | 4/2006 | Lee et al. |
| 2006/0006379 | A1 | 1/2006 | Lee et al. |
| 2008/0087884 | A1* | 4/2008 | Doi .................................. 257/40 |
| 2008/0251784 | A1* | 10/2008 | Tanaka et al. .................... 257/40 |

FOREIGN PATENT DOCUMENTS

| | | |
|---|---|---|
| WO | WO 00/79617 | 12/2000 |
| WO | WO 2005/070994 | 8/2005 |
| WO | WO 2006/038459 | 4/2006 |

OTHER PUBLICATIONS

Ando, S., et al. "n-Type Organic Field-Effect Transistors with Very High Electron Mobility Based on Thiazole Oligomers with Trifluoromethylphenyl Groups." J. Am. Chem. Soc., vol. 127 (2005): pp. 14996-14997.*

Mamada, M., et al. "n-Type Organic Field-Effect Transistors with High Electron Mobilities Based on Thiazole-Thiasolothiazole Conjugated Molecules." Chem. Mater., vol. 19 (2007): pp. 5404-5409.*

Organic and Polymeric Materials and Devices, *Materials Research Soc. Symp. Proc.* vol. 771, San Francisco, CA; pp. 157-169 (Apr. 22-25, 2003).

Garnier et al., "Molecular Engineering of Organic Semiconductors: Design of Self-Assembly Properties in Conjugated Thiophene Oligomers," *J. Am. Chem. Soc.*, vol. 115, pp. 8716-8721 (1993).

John K. Stille, "The Palladium-Catalyzed Cross-Coupling Reactions of Organotin Reagents with Organic Electrophiles," *Agnew Chem. Int. Ed. Engl.*, vol. 25, pp. 508-524 (1986).

Miyaura et al., "Palladium-Catalyzed Inter- and Intramolecular Cross-Coupling Reactions of B-Alkyl-9-borabicyclo[3.3.1]nonane Derivatives with 1-Halo-1-alkenes or Haloarenes, Syntheses of Functionalized Alkenes, Arenes, and Cycloalkenes via a Hydroboration-Coupling Sequence", *J. Am. Chem. Soc.*, vol. 111, pp. 314-321 (1989).

Yamamoto et al., "Preparation of π-Conjugated Poly(thiophene-2,5-diyl), Poly(p-phenylene), and Related Polymers Using Zerovalent Nickel Complexes, Linear Structure and Properties of the π-Conjugated Polymers", *Macrolmolecules*, vol. 25, pp. 1214-1223 (1992).

Van Pham et al., "Lithiation Reaction of 2,5-Dibromothiophene, NMR Spectra of 3-Substituted Derivatives", *J. Org. Chem.* vol. 49, pp. 5250-5253 (1984).

Genzer et al., "Creating Long-Lived Superhydrophobic Polymer Surfaces Through Mechanically Assembled Monolayers," *Science*, vol. 290, pp. 2130-2133 (Dec. 15, 2000).

European Search Report dated Jul. 28, 2009 in corresponding European Application No. 08150569.5.

Yamamoto et al., "π-conjugated and light emitting poly(4,4-dialkyl-2,2'-dithiazole-5,5'-diyl)s and their analogues comprised of electron-accepting five-membered rings, preparation, regioregular structure, face-to-face stacking, and electrochemical and optical properties", *Chem. Mater.*, v9, pp. 1217-1225 (1997).

Ando et al., "n-Type organic field-effect transistors with very high electron mobility based on thiazole oligomers with trufluoromethylphenyl groups", J. Am. Chem. Soc., v127, pp. 14996-14997 (2005).

Cao et al., "Synthesis and characterization of bis(3,4-ethylenedioxythiophene)-(4,4'-dialkyl-2,2'-bithiazole) co-oligomers for electronic applications", *Chem. Mater.*, v15, pp. 404-411 (2003).

* cited by examiner

COMPOSITION CONTAINING THIAZOLE RINGS, ORGANIC SEMICONDUCTOR POLYMER CONTAINING THE COMPOSITION, ORGANIC ACTIVE LAYER CONTAINING THE ORGANIC SEMICONDUCTOR POLYMER, ORGANIC THIN FILM TRANSISTOR CONTAINING THE ORGANIC ACTIVE LAYER, ELECTRONIC DEVICE CONTAINING THE ORGANIC THIN FILM TRANSISTOR AND METHOD OF PREPARING THE SAME

PRIORITY STATEMENT

This non-provisional application claims priority under 35 U.S.C. §119 to Korean Patent Application No. 2007-0007500, filed on Jan. 24, 2007, in the Korean Intellectual Property Office (KIPO), the entire contents of which are herein incorporated by reference.

BACKGROUND

1. Field

Example embodiments relate to a composition containing thiazole rings, an organic semiconductor polymer containing the composition, an organic active layer containing the organic semiconductor polymer, an organic thin film transistor (OTFT) containing the organic active layer, an electronic device containing the OTFT, and a method of preparing the same. Other example embodiments relate to a composition containing thiazole rings of a structure, which contains hetero arylene or arylene showing p-type semiconductor property in addition to thiophene showing p-type semiconductor property and thiazole rings showing n-type semiconductor property at a polymer main chain, to thereby exhibit increased charge carrier mobility and decreased blocking leakage current when applied to an organic thin film transistor, an organic semiconductor polymer containing the composition, an organic active layer containing the organic semiconductor polymer, an OTFT containing the organic active layer, an electronic device containing the OTFT, and a method of preparing the same.

2. Description of the Related Art

An organic thin film transistor (OTFT) may include a substrate, a gate electrode, an insulating layer, a source-drain electrode and a channel layer, and may be a bottom contact (BC) type or a top contact (TC) type. The bottom contact (BC) type may form the channel layer on the source-drain electrode, and the top contact (TC) type may have a metal electrode formed through mask deposition on the channel layer.

The channel layer of the OTFT has been commonly made of an inorganic semiconductor material, e.g., silicone (Si). However, the use of such inorganic-based material may be economically unfavorable and may require a high temperature-high vacuum process. Thus, the inorganic-based material has been replaced by an organic-based material, in accordance with enlargement, cost-reduction and softening requirements of a display.

Research on an organic semiconductor material for a channel layer of an OTFT is in progress, and the property of a transistor using the same has been reported. Representative examples of the small molecular or oligomer organic semiconductor material, which has been studied, may include melocyanine, pthalocyanine, perylene, pentacene, C60 and/or thiophene oligomer, and the related art demonstrates an organic semiconductor material showing increased charge carrier mobility of about 3.2~5.0 cm$^2$/Vs or more by using pentacene crystals. Further, an increased charge carrier mobility of about 0.01~0.1 cm$^2$/Vs and current on/off ratio may be possible by using an oligothiophene derivative. However, the above-described techniques mainly form a thin film depending upon a vacuum process.

There have been numerous reports for an OTFT using a thiophene-based polymer as a polymer material. Such an OTFT does not show as improved properties as that using a relatively small molecular material, but has an advantage in that it is possible to process a relatively large area at reduced costs through a solution process, e.g., printing technique. A polymer OTFT device experimentally prepared by using F8T2 polythiophene material may exhibit about 0.01~0.02 cm$^2$/Vs of charge carrier mobility. As described above, although the organic semiconductor polymer material exhibits relatively lower properties of a TFT device, e.g., charge carrier mobility, than pentacene which is the relatively small molecular material, such material has advantages in that it does not require increased operation frequency and may be economically used in the fabrication of a TFT.

However, in order to commercialize an OTFT, important parameters, e.g., increased current on/off ratio and charge carrier mobility, must be satisfied. Leakage current under a blocking (off) condition should be reduced as much as possible.

The related art discloses that the combination of an n-type inorganic semiconductor material and a p-type organic semiconductor material as an active layer improves the parameters of an OTFT device. However, this process is still relatively difficult in mass-production because it is not different from the existing silicone-based TFT process requiring deposition. The related art also teaches an OTFT device having about 0.01~0.04 cm$^2$/Vs of charge carrier mobility which is prepared by using regioregular poly(3-hexylthiophene)(P3HT). However, because the representative regioregular poly(3-hexylthiophene) (P3HT) shows relatively increased charge carrier mobility of about 0.01 cm$^2$/Vs, but its current on/off ratio is lower than 400 due to its increased blocking leakage current (about $10^{-9}$ A or more), its application to an electrical device may be limited.

SUMMARY

Therefore, example embodiments have been made in view of the above problems of the related art, and example embodiments provide a composition used in an organic semiconductor polymer of an OTFT, which contains hetero arylene or arylene showing a p-type semiconductor property, in addition to thiophene showing a p-type semiconductor property and thiazole rings showing a n-type semiconductor property at a polymer main chain, to thereby exhibit increased charge carrier mobility and decreased blocking leakage current.

Example embodiments also provide an organic semiconductor polymer containing the composition, an organic active layer containing the organic semiconductor polymer, an organic thin film transistor (OTFT) containing the organic semiconductor polymer which satisfies the conditions of both increased charge carrier mobility and decreased blocking leakage current by using the organic semiconductor polymer material as an organic active layer, an electronic device containing the OTFT, and a method of preparing the same.

In accordance with example embodiments, there is provided a composition including two thiazole rings separated by a spacer group $D_1$ and represented by the following Formula 1:

[Formula 1]

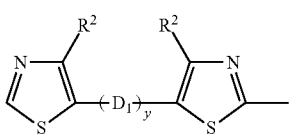

wherein $R^2$ is hydrogen, hydroxy, linear, branched or cyclic $C_{1\sim20}$ alkyl, $C_{1\sim20}$ alkoxyalkyl, or linear, branched or cyclic $C_{1\sim16}$ alkoxy; $D_1$ is $C_{2\sim20}$ hetero arylene or $C_{6\sim30}$ arylene; and v is an integer ranging from 1 to 4.

The hetero arylene may be a 5-membered hetero arylene substituted with one or more elements selected from the group consisting of S, N—H, O and Se. The hetero arylene and arylene may be substituted with one or more elements selected from the group consisting of hydroxy, linear, branched or cyclic $C_1\sim C_{20}$ alkyl, $C_1\sim C_{20}$ alkoxyalkyl, linear, branched or cyclic $C_1\sim C_{16}$ alkoxy, F, Br, Cl and I. The hetero arylene and arylene may be selected from the compounds represented by the following Formula 2:

[Formula 2]

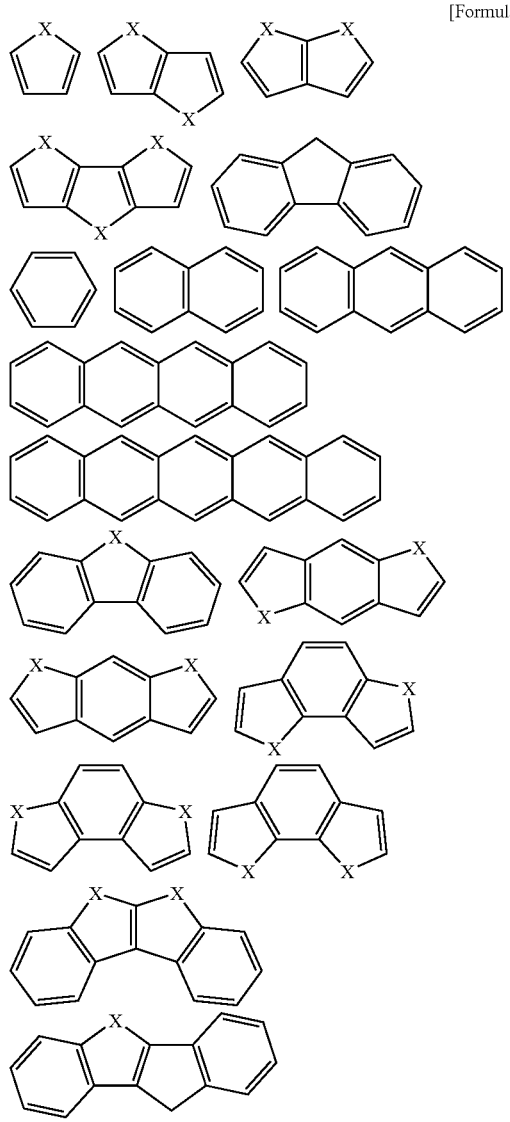

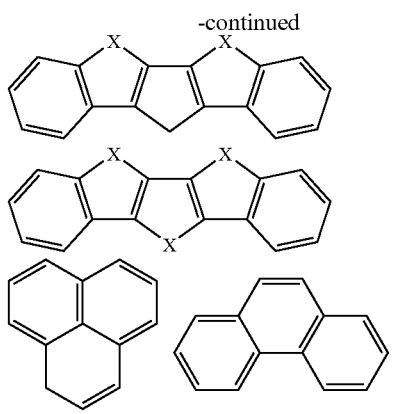

wherein X is S, N—H, O or Se.

In accordance with example embodiments, there is provided an organic semiconductor polymer including the composition of example embodiments, two thiophene rings and a spacer group $D_2$, and represented by the following Formula 3:

[Formula 3]

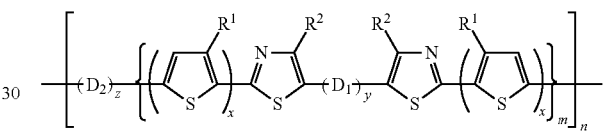

wherein $R^1$ is hydrogen, hydroxy, linear, branched or cyclic $C_1\sim C_{20}$ alkyl, $C_1\sim C_{20}$ alkoxyalkyl, or linear, branched or cyclic $C_1\sim C_{16}$ alkoxy; $D_2$ is $C_2\sim C_{20}$ hetero arylene or $C_6$-$C_{30}$ arylene; x is an integer ranging from 2 to 6; y is an integer ranging from 1 to 4; z is an integer ranging from 0 to 4; m is an integer ranging from 1 to 6; and n is an integer ranging from 4 to 100.

Each $R^1$ may be the same or different from each other and $D_1$ and $D_2$ may be the same or different from each other. The hetero arylene may be a 5-membered hetero arylene substituted with one or more elements selected from the group consisting of S, N—H, C and Se. The hetero arylene and arylene may be substituted with one or more elements selected from the group consisting of hydroxy, linear, branched or cyclic $C_1\sim C_{20}$ alkyl, $C_1\sim C_{20}$ alkoxyalkyl, linear, branched or cyclic $C_1\sim C_{16}$ alkoxy, F, Br, Cl and I. The hetero arylene and arylene may be selected from the compounds represented by the following Formula 2:

[Formula 2]

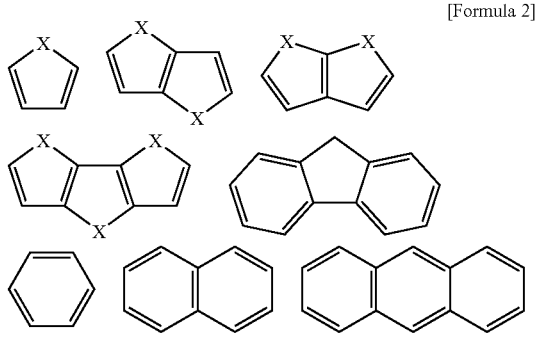

-continued

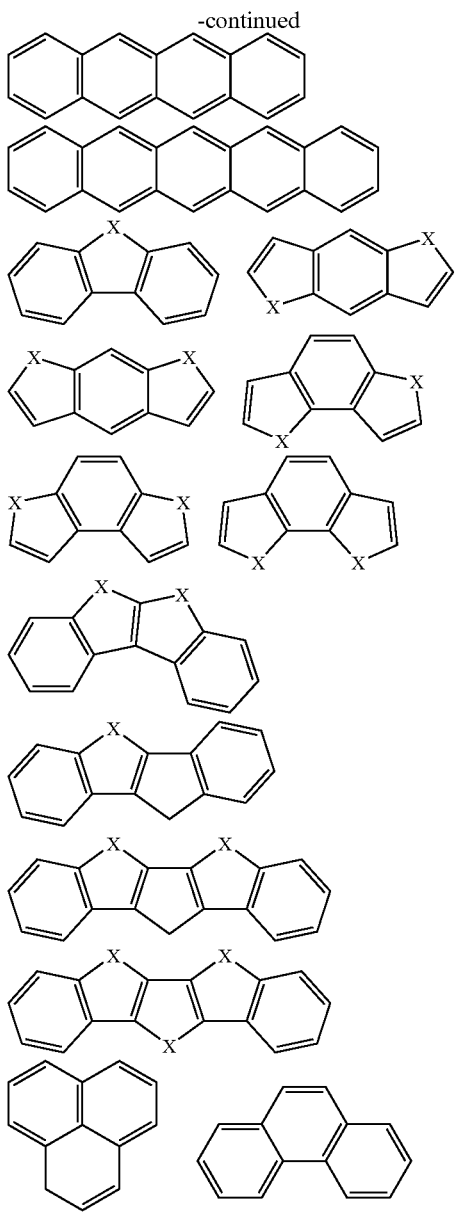

wherein X is S, N—H, O or Se.

The number average molecular weight of the organic semiconductor polymer may range from about 5,000 to about 100,000, for example, about 10,000 to about 100,000.

In accordance with example embodiments, there is provided an organic active layer including the organic semiconductor polymer of example embodiments. The organic active layer may be formed using a process selected from the group consisting of screen printing, printing, spin coating, dipping and ink spraying.

In accordance with example embodiments, there is provided an organic thin film transistor including a substrate, a gate electrode, a gate insulating layer, an active layer, and source/drain electrodes, wherein the active layer is the organic active layer of example embodiments. The organic thin film transistor may have a top contact or a bottom contact structure. The gate electrode and the source/drain electrodes may be made of gold(Au), silver(Ag), aluminum(Al), nickel (Ni), or indium tin oxide(ITO). The gate insulating layer may be made of a ferroelectric insulator selected from the group consisting of $Ba_{0.33}Sr_{0.66}TiO_3$ BST(barium strontium titanate), $Al_2O_3$, $Ta_2O_5$, $La_2O_5$, $Y_2O_3$ and $TiO_2$; an inorganic insulator selected from the group consisting of $PbZr_{0.33}Ti_{0.66}O_3$ (PZT), $Bi_4Ti_3O_{12}$, $BaMgF_4$, $SrBi_2$ (TaNb) 209, $Ba(ZrTi)O_3$(BZT), $BaTiO_3$, $SrTiO_3$, $Bi_4Ti_3Ol_2$, $SiO_2$, SiNx and AlON; and an organic insulator selected from the group consisting of polyimide, benzocyclobutane(BCB), parylene, polyacrylate, polyvinylalcohol and polyvinylphenol. The substrate may be made of glass, polyethylenenaphthalate (PEN), polyethyleneterephthalate (PET), polycarbonate, polyvinylalcohol, polyacrylate, polyimide, polynorbornene, or polyethersulfone (PES).

In accordance with example embodiments, there is provided an electronic device including the OTFT of example embodiments. The electronic device may be a photovoltaic device, an organic light-emitting diode (LED) or a sensor.

In accordance with example embodiments, there is provided a method for preparing the organic semiconductor polymers containing thiazole rings including polymerizing a monomer represented by the following Formula 3, or copolymerizing the monomer of Formula 3 with a monomer represented by the following Formula 4:

[Formula 3]

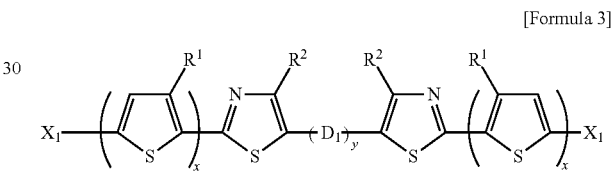

wherein $R^1$ and $R^2$ are independently hydrogen, hydroxy, linear, branched or cyclic $C_1$~$C_{20}$ alkyl, $C_1$~$C_{20}$ alkoxyalkyl, or linear, branched or cyclic $C_1$~$C_{16}$ alkoxy; plural $R^1$ is the same as or different from each other; and $D_1$ is $C_2$~$C_{20}$ hetero arylene or $C_6$~$C_{30}$ arylene, and the hetero arylene and arylene are substituted with one or more elements selected from the group consisting of hydroxy, linear, branched or cyclic $C_1$~$C_{20}$ alkyl, $C_1$~$C_{20}$ alkoxyalkyl, linear, branched or cyclic $C_1$~$C_{16}$ alkoxy, F, Br, Cl and I; x is an integer ranging from 2 to 6; y is an integer ranging from 1 to 4; and $X_1$ is an halogen atom such as Br, Cl or I, trialkyltin or boran.

$$Y^3-(D)_b-Y^4$$ [Formula 4]

wherein D is defined as in $D_1$ of Formula 2; D and $D_1$ is the same as or different from each other; $Y^3$ and $Y^4$ are independently an halogen atom such as Br, Cl or I, trialkyltin or boran; and b is an integer ranging from 1 to 4.

BRIEF DESCRIPTION OF THE DRAWINGS

Example embodiments will be more clearly understood from the following detailed description taken in conjunction with the accompanying drawings.

FIGS. 1-2 are sectional diagrams schematically illustrating a top contact OTFT device and a bottom contact OTFT device, respectively, of example embodiments;

FIG. 3 is a current-transfer characteristic curve of an organic semiconductor polymer containing thiazole rings (Poly-4) prepared in Preparation Example 5 of example embodiments.

Figure 1:
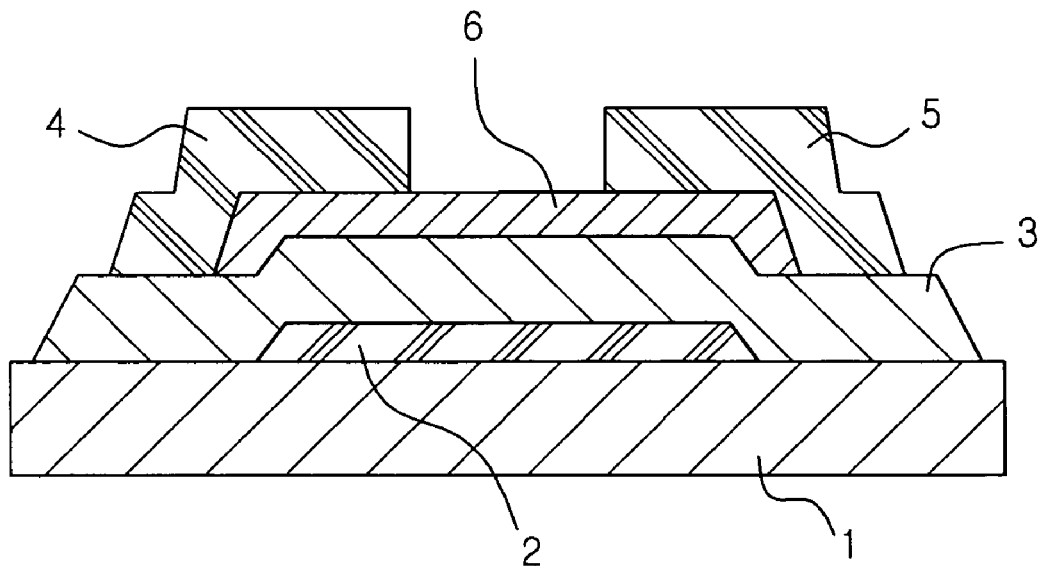
FIGS. 1-3 represent non-limiting, example embodiments as described herein.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF EXAMPLE EMBODIMENTS

Hereinafter, example embodiments will be explained in more detail with reference to the accompanying drawings. Reference now should be made to the drawings, in which the same reference numerals are used throughout the different drawings to designate the same or similar components. In the drawings, the thicknesses and widths of layers are exaggerated for clarity. Example embodiments may, however, be embodied in many different forms and should not be construed as limited to the example embodiments set forth herein. Rather, these example embodiments are provided so that this disclosure will be thorough and complete, and will fully convey the scope of example embodiments to those skilled in the art.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In accordance with example embodiments, there is provided a composition including two thiazole rings separated by a spacer group $D_1$ and represented by the following Formula 1:

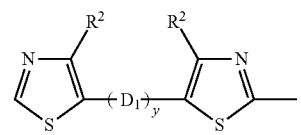

[Formula 1]

wherein $R^2$ is hydrogen, hydroxy, linear, branched or cyclic $C_{1\sim20}$ alkyl, $C_{1\sim20}$ alkoxyalkyl, or linear, branched or cyclic $C_{1\sim16}$ alkoxy; and $D_1$ is $C_{2\sim20}$ hetero arylene or $C_{6\sim30}$ arylene.

The hetero arylene may be a 5-membered hetero arylene substituted with one or more elements selected from the group consisting of S, N—H, O and Se. The hetero arylene and arylene may be substituted with one or more elements selected from the group consisting of hydroxy, linear, branched or cyclic $C_1\sim C_{20}$ alkyl, $C_1\sim C_{20}$ alkoxyalkyl, linear, branched or cyclic $C_1$~$C_{16}$ alkoxy, F, Br, Cl and I. The hetero arylene and arylene may be selected from the compounds represented by the following Formula 2:

[Formula 2]

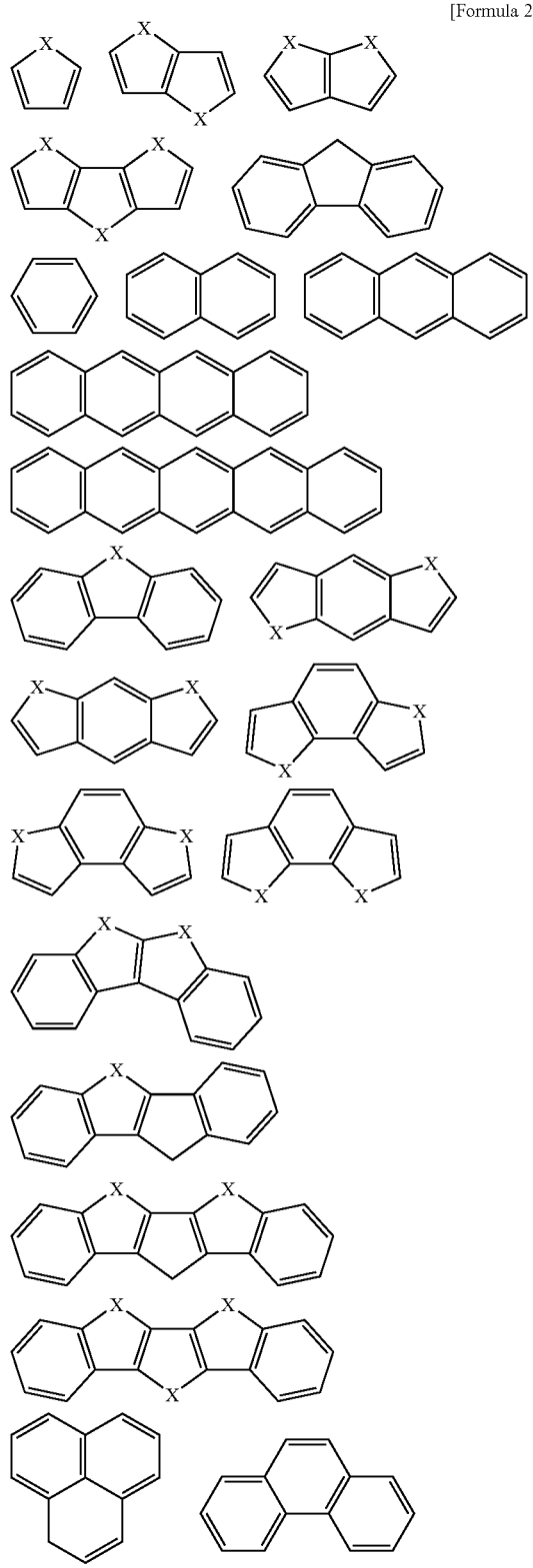

wherein X is S, N—H, O or Se.

Organic semiconductor polymers containing thiazole rings according to example embodiments may have a structure represented by the following Formula 3:

[Formula 3]

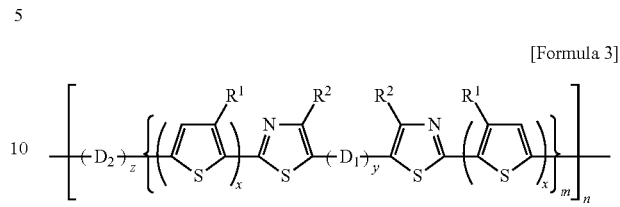

wherein $R^1$ and $R^2$ are independently hydrogen, hydroxy, linear, branched or cyclic $C_{1-20}$ alkyl, $C_{1-20}$ alkoxyalkyl, or linear, branched or cyclic $C_{1-16}$ alkoxy; plural $R^1$ may be the same as or different from each other; $D_1$ and $D_2$ may be the same as or different from each other; $D_1$ and $D_2$ are independently $C_{2-20}$ hetero arylene or $C_{6-30}$ arylene; x is an integer ranging from about 2 to about 6; y is an integer ranging from about 1 to about 4; z is an integer ranging from about 0 to about 4; m is an integer ranging from about 1 to about 6; and n is an integer ranging from about 4 to about 100.

The hetero arylene may be a 5-membered hetero arylene substituted with one or more elements selected from the group consisting of S, N—H, O and Se, and the hetero arylene and arylene may be substituted with one or more elements selected from the group consisting of hydroxy, linear, branched or cyclic $C_1$~$C_{20}$ alkyl, $C_1$~$C_{20}$ alkoxyalkyl, linear, branched or cyclic $C_1$~$C_{16}$ alkoxy, F, Br, Cl and I. The hetero arylene and arylene may be selected from the compounds represented by the following Formula 2:

[Formula 2]

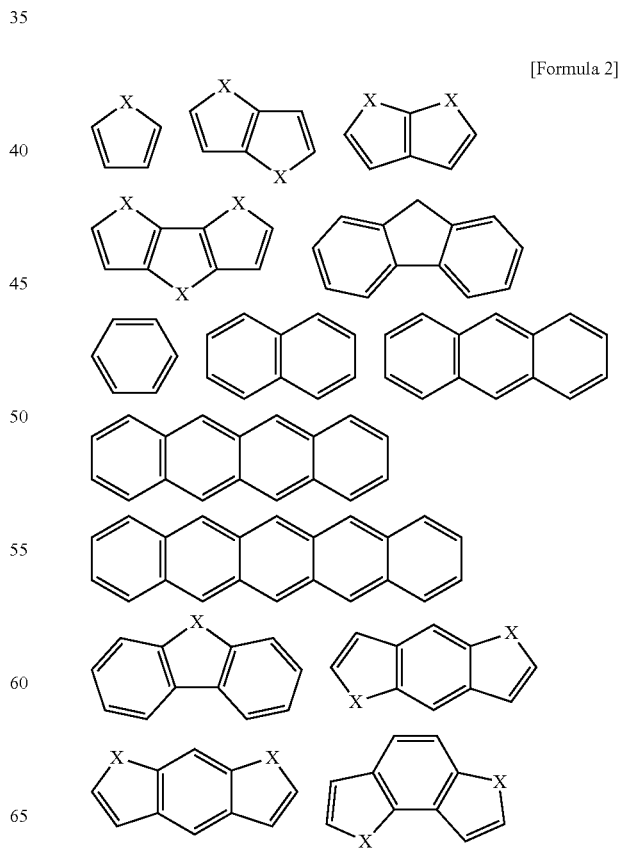

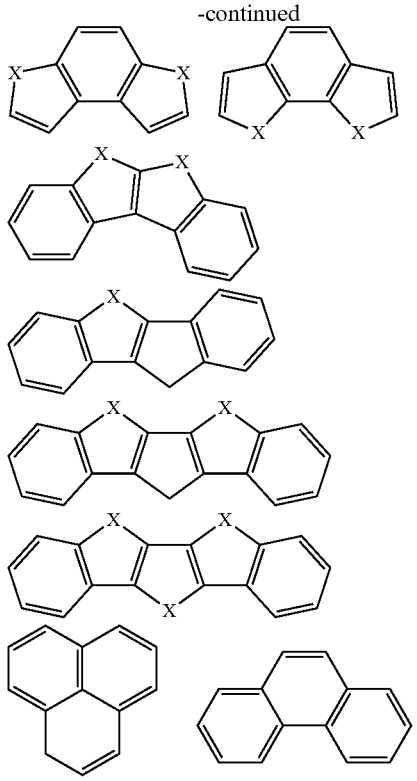

wherein X is S, N—H, O or Se.

In accordance with example embodiments, there is provided an organic active layer including the organic semiconductor polymer of example embodiments. The organic active layer may be formed using a process selected from the group consisting of screen printing, printing, spin coating, dipping and ink spraying.

In accordance with example embodiments, there is provided an organic thin film transistor including a substrate, a gate electrode, a gate insulating layer, an active layer, and source/drain electrodes, wherein the active layer is the organic active layer of example embodiments. The organic thin film transistor may have a top contact or a bottom contact structure. The gate electrode and the source/drain electrodes may be made of gold(Au), silver(Ag), aluminum(Al), nickel (Ni), or indium tin oxide(ITO). The gate insulating layer may be made of a ferroelectric insulator selected from the group consisting of $Ba_{0.33}Sr_{0.66}TiO_3$ BST(barium strontium titanate), $Al_2O_3$, $Ta_2O_5$, $La_2O_5$, $Y_2O_3$ and $TiO_2$; an inorganic insulator selected from the group consisting of $PbZr_{0.33}Ti_{0.66}O_3$ (PZT), $Bi_4Ti_3O_{12}$, $BaMgF_4$, $SrBi_2$ $(TaNb)_2O_9$, $Ba(ZrTi)O_3(BZT)$, $BaTiO_3$, $SrTiO_3$, $Bi_4Ti_3O_{12}$, $SiO_2$, SiNx and AlON; and an organic insulator selected from the group consisting of polyimide, benzocyclobutane(BCB), parylene, polyacrylate, polyvinylalcohol and polyvinylphenol. The substrate may be made of glass, polyethylenenaphthalate (PEN), polyethyleneterephthalate (PET), polycarbonate, polyvinylalcohol, polyacrylate, polyimide, polynorbornene, or polyethersulfone (PES).

In accordance with example embodiments, there is provided an electronic device including the OTFT of example embodiments. The electronic device may be a photovoltaic device, an organic light-emitting diode (LED) or a sensor.

The organic semiconductor polymers containing thiazole rings represented by Formula 1 may be prepared by polymerizing a monomer represented by the following Formula 3, or co-polymerizing the monomer of Formula 3 with a monomer represented by the following Formula 4:

[Formula 3]

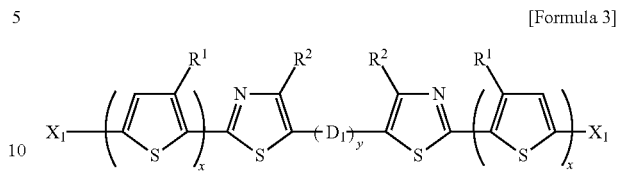

wherein $R^1$ and $R^2$ are independently hydrogen, hydroxy, linear, branched or cyclic $C_{1\sim20}$ alkyl, $C_{1\sim20}$ alkoxyalkyl, or linear, branched or cyclic $C_{1\sim16}$ alkoxy; plural $R^1$ may be the same as or different from each other; and $D_1$ is $C_{2\sim20}$ hetero arylene or $C_{6\sim30}$ arylene, and the hetero arylene and arylene may be substituted with one or more elements selected from the group consisting of hydroxy, linear, branched or cyclic $C_{1\sim20}$ alkyl, $C_{1\sim20}$ alkoxyalkyl, linear, branched or cyclic $C_{1\sim16}$ alkoxy, F, Br, Cl and I; x is an integer ranging from about 2 to about 6; y is an integer ranging from about 1 to about 4; and $X_1$ is an halogen atom, e.g., Br, Cl or I, trialkyltin or boran.

[Formula 4]

wherein D may be defined as in $D_1$ of Formula 2; D and $D_1$ may be the same as or different from each other; $Y^3$ and $Y^4$ are independently an halogen atom, e.g., Br, Cl or I, trialkyltin or boran; and b is an integer ranging from about 1 to about 4.

The aromatic compounds represented by Formula 4 among the above-described monomers may be exemplified by compounds selected from the group represented by the following Formula 5, but are not limited thereto:

[Formula 5]

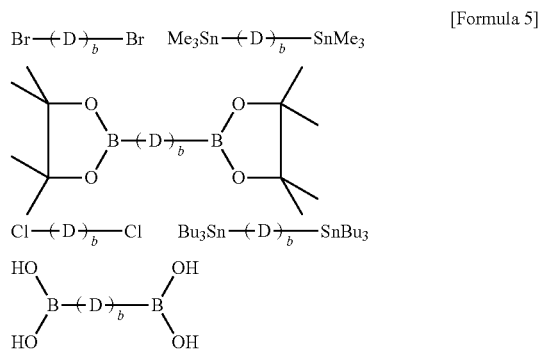

wherein D and b are the same as defined in Formula 4.

The organic semiconductor polymers containing thiazole rings of Formula 1 of example embodiments may be synthesized by co-polymerizing the monomer of Formula 3 with the monomer of Formula 4 according to the following Reaction Scheme 1. However, there is no limitation on a polymerization method.

[Reaction Scheme 1]

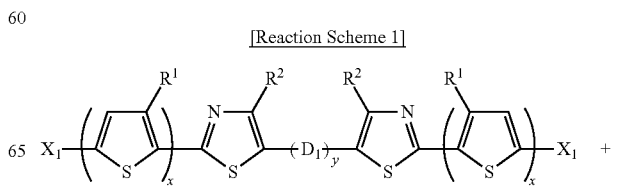

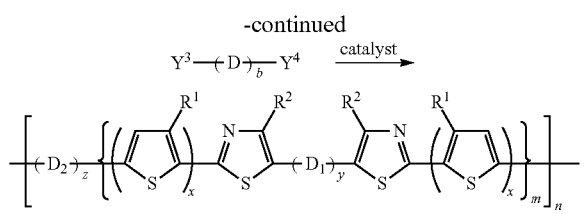

wherein $R^1$, $R^2$, D, $D_1$, $D_2$, x, y, b, $Y^1$, $Y^2$, $Y^3$, $Y^4$, and $X_1$ are the same as defined in Formulae 1 to 3 and Reaction Scheme 1, and D is $D_1$ or $D_2$.

The organic semiconductor polymers containing thiazole rings according to example embodiments may be synthesized according to a method using a palladium catalyst represented by the following Formula 6 or a nickel catalyst represented by the following Formula 7:

   [Formula 6]

wherein L is a ligand selected from the group consisting of triphenylphosphin($PPh_3$), triphenylallicin($AsPh_3$) and triphenylphosphite$(OPh)_3$.

   [Formula 7]

wherein L' is a ligand selected from the group consisting of 1,5-cyclooctadiene, 1,3-diphenylphosphinopropane, 1,2-bis (diphenylphosphino)ethane and 1,4-diphenylphosphinobutane. Representative examples of the nickel(0) catalyst may include bis(1,5-cyclooctadiene) nickel(0) compound[Ni$(COD)_2$], and representative examples of the nickel(II) catalyst may include 1,3-diphenylphosphinopropane nickel (II) chloride [Ni (dppp) $Cl_2$] and 1,2-bis(diphenylphosphino) ethane nickel(II) chloride [Ni (dppe) $Cl_2$]

Further, a solvent suitable for the polymerization of example embodiments may include toluene, dimethylformamide(DMF), tetrahydrofuran(THF) and/or N-methylpyrrolidinone(NMP). A condensation reaction may be conducted at a temperature ranging from about 60° C. to about 120° C., under a nitrogen atmosphere for about 5 hours to about 12 hours.

Organic semiconductor polymers containing thiazole rings may be prepared by polymerizing only the monomer represented by Formula 3, without using the monomer represented by Formula 4 in Reaction Scheme 1.

Among the monomers, the organic compounds containing thiazole rings represented by Formula 3 may be synthesized through a condensation reaction using organic metal catalysts represented by the following Formulae 6 and 7, and its typical reaction may be exemplified by the following Reaction Scheme 2:

[Reaction Scheme 2]

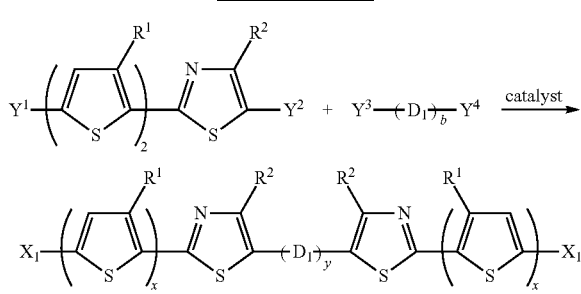

wherein $R^1$, $R^2$, $D_1$, x, y, $Y^3$, $Y^4$, and $X_1$ are the same as defined in Formula 1; a is an integer ranging from about 2 to about 6; and $Y^1$ and $Y^2$ are independently an halogen atom, e.g., Br, Cl or I, trialkyltin or boran.

Tetrakis (triphenylphosphine) palladium(0) [Pd$(PPh_3)_4$] may be used as a palladium(0) catalyst in the amount of about 0.2 to about 10 mole % based on the total amount of monomers.

Representative examples of the organic compounds containing thiazole rings represented by Formula 3 may include compounds selected from the group represented by the following Formula 8:

[Formula 8]

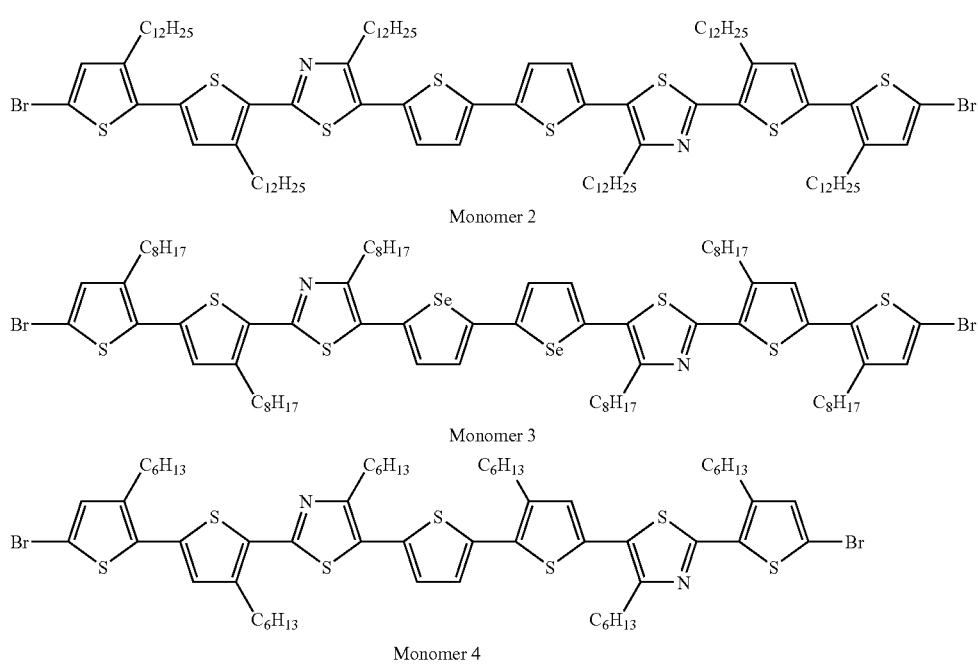

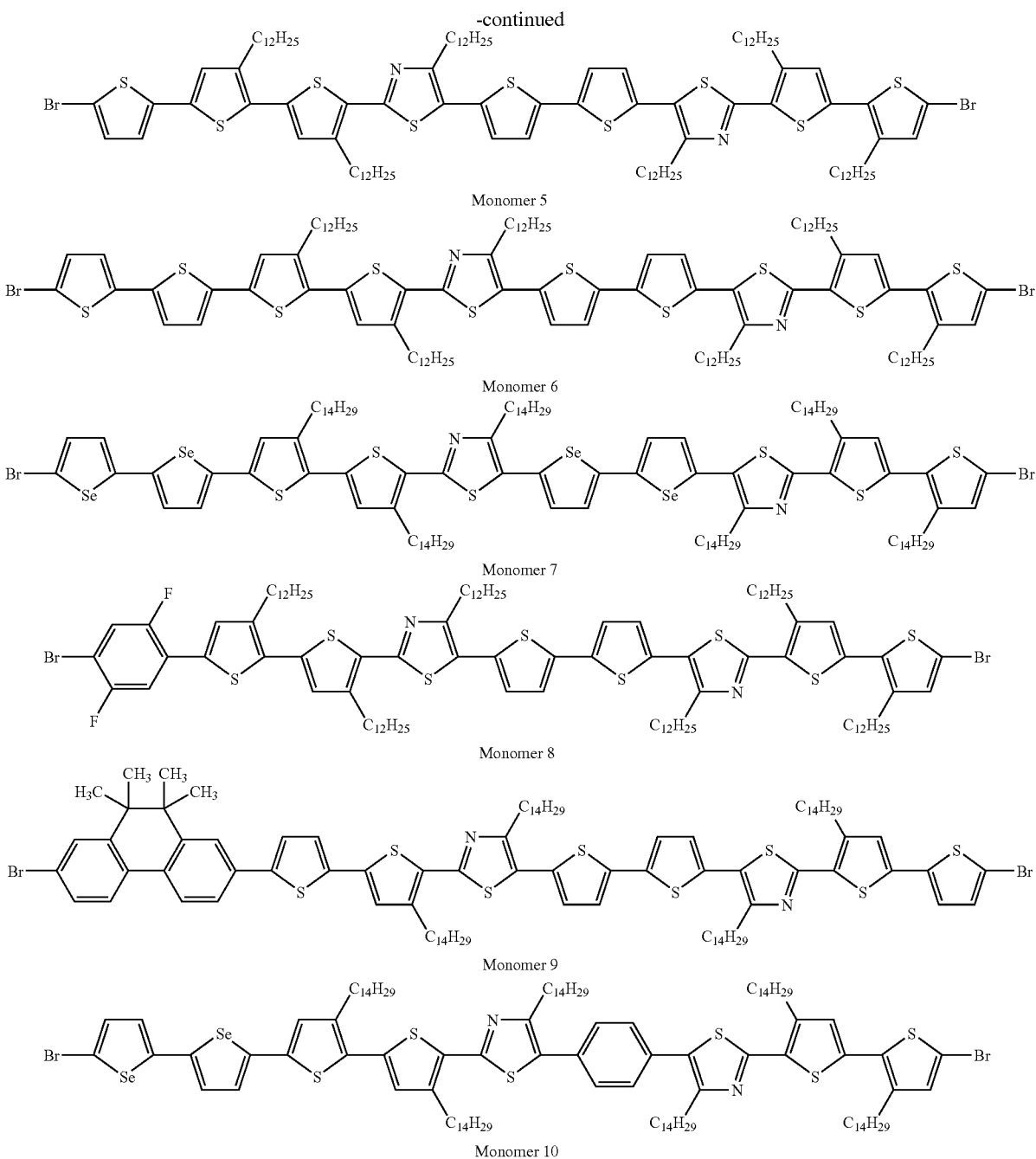
Representative examples of the organic semiconductor polymers of Formula 1 according to example embodiments may include compounds selected from the group represented by the following Formula 9, but are not limited thereto:
[Formula 9]
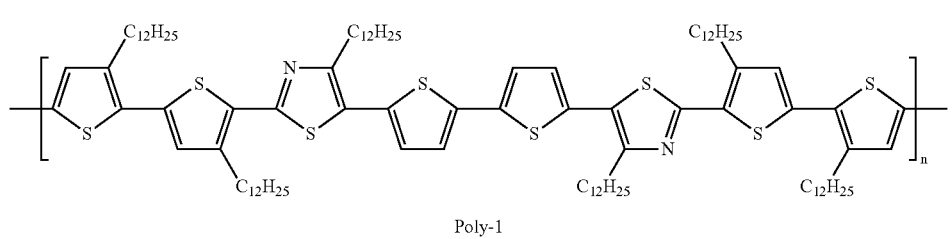

-continued
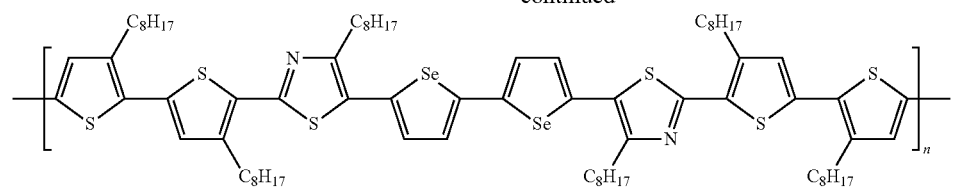
Poly-2
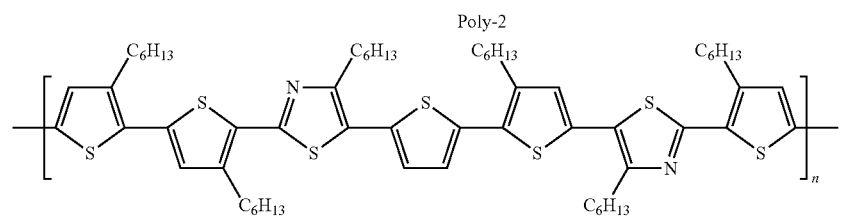
Poly-3
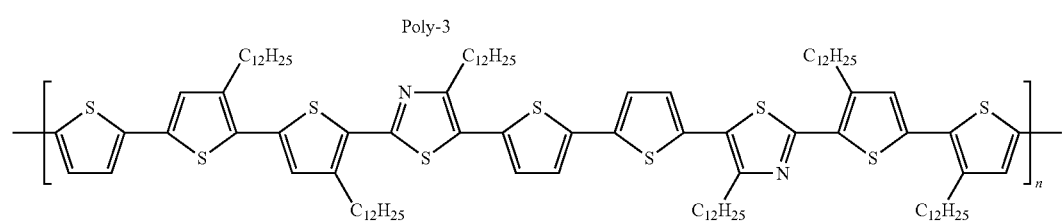
Poly-4
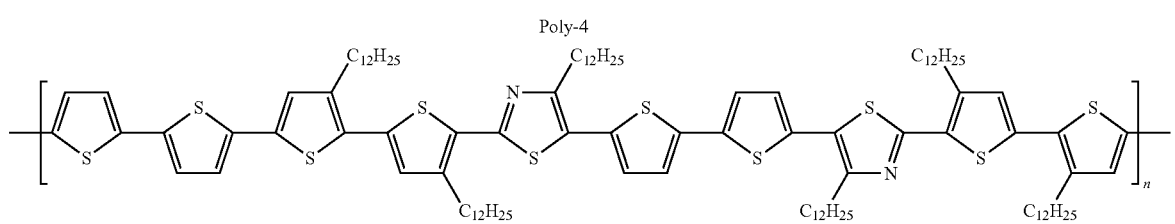
Poly-5
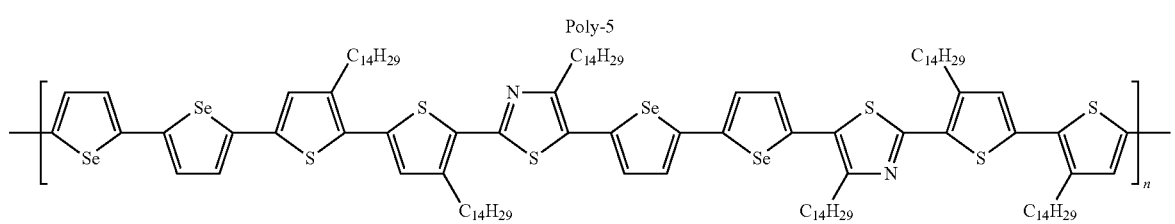
Poly-6
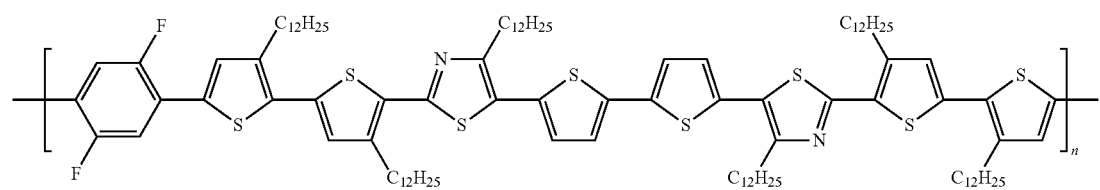
Poly-7
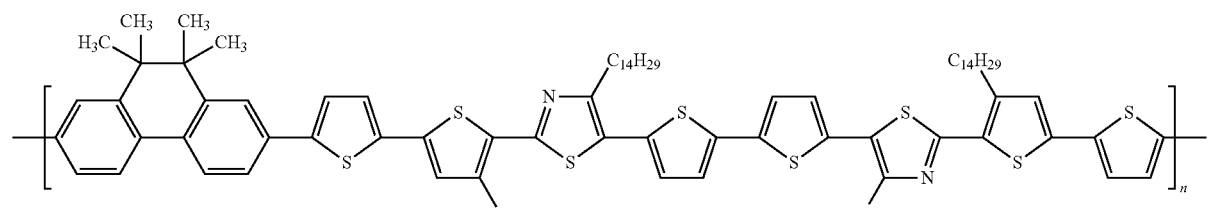
Poly-8

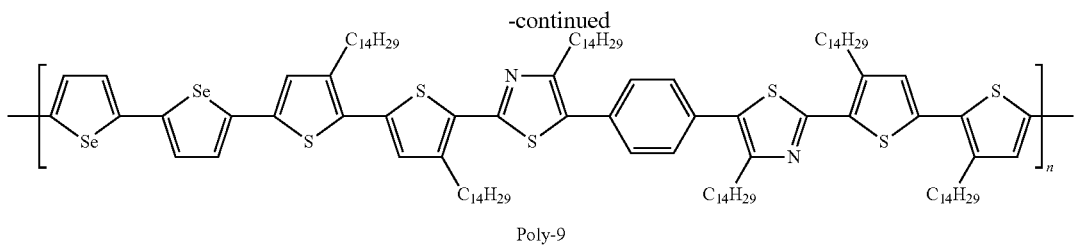

Poly-9 wherein n is an integer ranging from about 4 to about 100.

The number average molecular weight of the organic semiconductor polymer according to example embodiments may range from about 5,000 to about 100,000, for example, about 10,000 to about 100,000.

The composition containing thiazole rings and a spacer group $D_1$, and organic semiconductor polymers containing the composition, two thiophene groups and a spacer group $D_2$, according to example embodiments, may exhibit increased solubility to an organic solvent, coplanarity, processibility and an improved thin film property, and, when applied to an OTFT as an active layer, show increased charge carrier mobility and decreased blocking leakage current.

The composition containing thiazole rings and a spacer group $D_1$, and organic semiconductor polymers containing the composition, two thiophene groups and a spacer group $D_2$, according to example embodiments, may be used as a core element, e.g., charge generating and moving layers in electronic devices of a photovoltaic device, an organic light-emitting diode (LED) and/or a sensor, but may not be limited thereto. Because a conventional structure of such an electronic device is well-known in the art, a detailed description thereof is omitted here for simplicity.

Further, composition containing thiazole rings and a spacer group $D_1$, and organic semiconductor polymers containing the composition, two thiophene groups and a spacer group $D_2$, according to example embodiments, may be used as an organic semiconductor material forming an organic active layer, thereby manufacturing an OTFT device. The organic active layer may be formed through screen printing, printing, spin coating, dipping and/or ink spraying, but may not be limited thereto.

Figure 2:
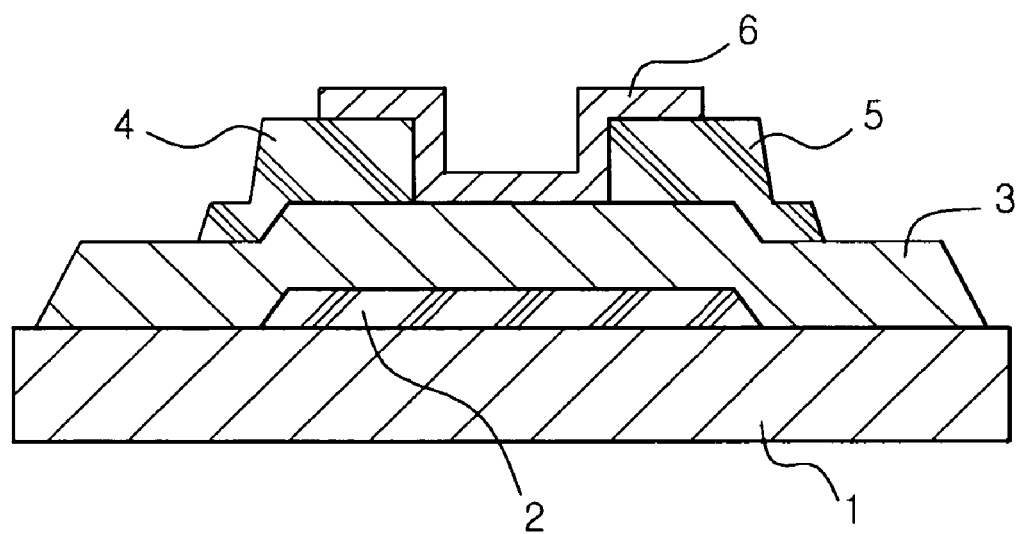

Such an OTFT device may have a top contact structure which includes a substrate 1, a gate electrode 2, a gate insulating layer 3, an active layer 6, and source/drain electrodes 4, 5, as in FIG. 1 or a bottom contact structure which includes a substrate 1, a gate electrode 2, a gate insulating layer 3, source/drain electrodes 4, 5, and an active layer 6, as in FIG. 2, but are not limited thereto.

The gate insulating layer constituting the OTFT device may be prepared by using an insulator having a high dielectric constant which is typically used in the art. Representative examples of the insulating layer may include a ferroelectric insulator selected from the group consisting of $Ba_{0.33}Sr_{0.66}TiO_3$ BST(barium strontium titanate), $Al_2O_3$, $Ta_2O_5$, $La_2O_5$, $Y_2O_3$ and $TiO_2$; an inorganic insulator selected from the group consisting of $PbZr_{0.33}Ti_{0.66}O_3$(PZT), $Bi_4Ti_3O_{12}$, $BaMgF_4$, $SrBi_2(TaNb)_2O_9$, $Ba(ZrTi)O_3$(BZT), $BaTiO_3$, $SrTiO_3$, $Bi_4Ti_3O_{12}$, $SiO_2$, SiNx and AlON; and an organic insulator selected from the group consisting of polyimide, benzocyclobutane(BCB), parylene, polyacrylate, polyvinyalcohol and polyvinylphenol, but are not limited thereto.

Further, the gate and source-drain electrodes constituting the OTFT device may be prepared by using a metal which is generally used in the art. Representative examples of the metal may include gold(Au), silver(Ag), aluminum(Al), nickel(Ni) and/or indium tin oxide(ITO), but are not limited thereto.

Additionally, the substrate constituting the OTFT device may be made of glass, polyethylenenaphthalate(PEN), polyethyleneterephthalate(PET), polycarbonate, polyvinylalcohol, polyacrylate, polyimide, polynorbornene and/or polyethersulfone(PES), but is not limited thereto.

Example embodiments will be described in more detail with reference to the following examples. However, these examples are given for the purpose of illustration and are not to be construed as limiting the scope of example embodiments.

Preparation Example 1

Synthesis of Compound 5

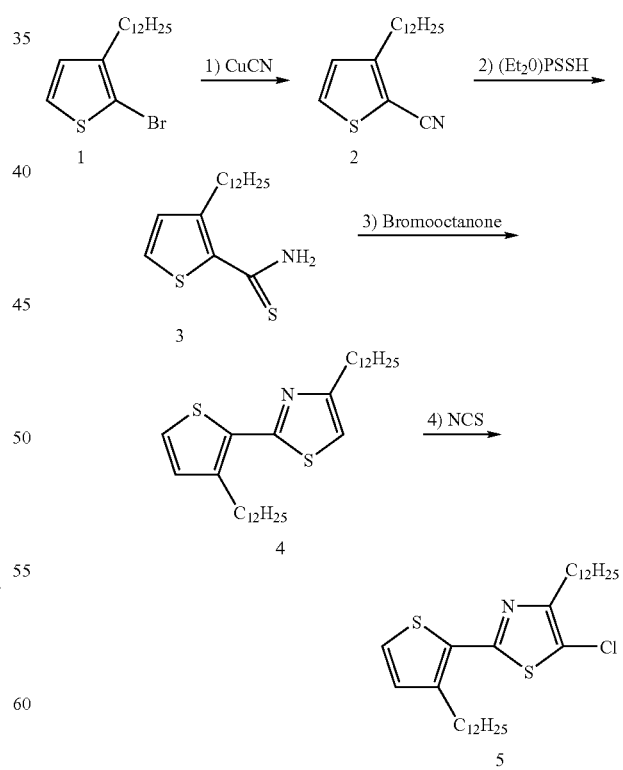

2) $(Et_2O)PSSH$ = dithiophosphoric acid O,O′-diethylether

About 20.0 g (about 81 mmol) of 2-bromo-3-dodecylthiophene(1) was reacted with a relatively large amount of copper cyanide(CuCN) to obtain 2-cyano-3-dodecylthiophene (yield: about 5.3 g, about 34%). The resulting compound was reacted with a relatively large amount (about 2.5 equivalents) of a THF solution of dithiophosphoric acid O,O'-diethylether for about 12 hours with heating. Thus, the obtained 2-thioamino-3-dodecylthiophene (compound 3)(yield: about 2.9 g, about 45%) was reacted with about 1.2 equivalents of bromooctanone to obtain 2-thiazole(3'-dodecyl)-3-dodecylthiphene(compound 4)(yield: about 1.4 g, about 32%). The compound 4 was reacted with NBS(N-bromosuccinimide), to thereby obtain an organic compound 5 (yield: about 1.32 g, about 82%) containing a thizaole ring. The $^1$H-NMR result of the compound 5 is as follows.

$^1$H-NMR (300 MHz, CDCl$_3$) δ (ppm) 0.89 (6H), 1.35 (12H), 1.68 (4H), 2.73 (2H), 2.83 (2H), 6.92 (1H), 7.26 (1H).

Preparation Example 2

Synthesis of Compound 6

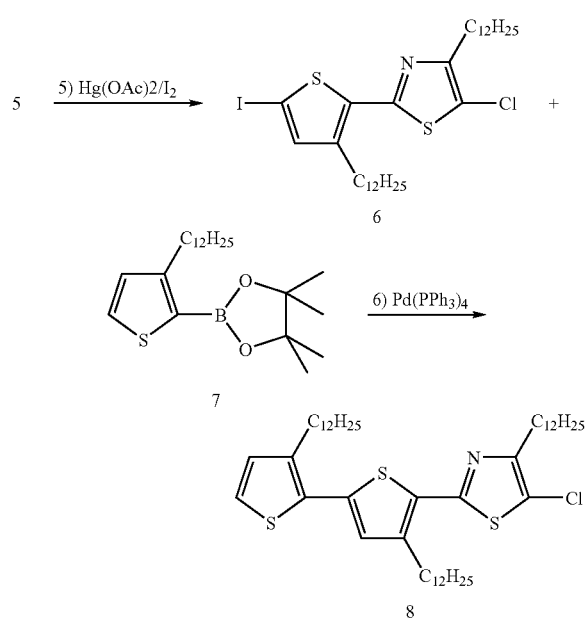

The compound 5 (about 120 g, about 223 mmol) was added to an about 3 L three-neck round bottom flask and dissolved in a mixture of CHCl$_3$ and AcOH (about 600 ml: about 600 ml). After Hg(OAc)$_2$ (about 42.6 g, about 134 mmol) was added thereto and the mixture was agitated for about 20 minutes, iodide (about 62.2 g, about 245 mmol) was gently added to the mixture and reacted for about 3 hours. After the reaction was completed, the reaction solution was filtered to remove red precipitates. An organic layer thus separated was successively washed with H$_2$O (about 500 ml), saturated sodium carbonate(NaHCO$_3$) solution (about 500 ml, about three times), sodium thiosulfate(Na$_2$S$_2$O$_3$) (about 500 ml) and brine (about 500 ml), and subjected to drying with magnesium sulfate, filtration and concentration. The concentrated organic layer was purified with a column using a hexane solvent, to thereby obtain an organic compound 6 (about 134 g, yield: about 90%). The $^1$H-NMR result of the organic compound 6 is as follows.

$^1$H NMR (300 MHz, CDCl$_3$) δ0.88 (t, 6H), 1.26 (m, 36H), 1.65 (m, 4H), 2.73 (m, 4H), 7.07 (s, 1H)

Preparation Example 3

Synthesis of Compound 8 Shown in Reaction Scheme 4

After the compound 6 (about 4.72 g, about 14.2 mmol) synthesized in Preparation Example 2 and the same amount of a compound 7 (about 14.2 mmol) was added to an about 3 L three-neck round bottom flask and dissolved in tetrahydrofuran(THF, about 50 ml), a palladium catalyst(Pd(PPh$_3$)$_4$, about 0.64 g, about 2.8 mmol)) and toluene (about 60 ml) were added thereto and the mixture was reacted for about 2 hours under reflux. After hexane (about 200 ml) was added to the reaction solution and the resulting mixture was washed with water (about 100 ml), an organic layer was dried with magnesium sulfate, filtered and concentrated. The concentrated organic layer was then added to an about 2 L round bottom flask and dissolved in methylene chloride (CH$_2$Cl$_2$, about 80 ml). In succession, the organic layer was dried with magnesium sulfate, filtered and concentrated, and then purified with a column using a hexane/chloroform solvent, to thereby obtain an organic compound 8 as a yellow solid (about 4.4 g, yield: about 27%). The $^1$H-NMR result of the organic compound 8 is as follows.

$^1$H NMR (300 MHz, CDCl$_3$) δ 0.88 (t, 9H), 1.26 (m, 54H), 1.64 (m, 6H), 2.79 (m, 6H), 6.94 (d, 2H), 7.19 (d, 1H)

Preparation Example 4

Synthesis of an Organic Compound Containing Thiazole Rings (Monomer-2) Using Reaction Scheme 2

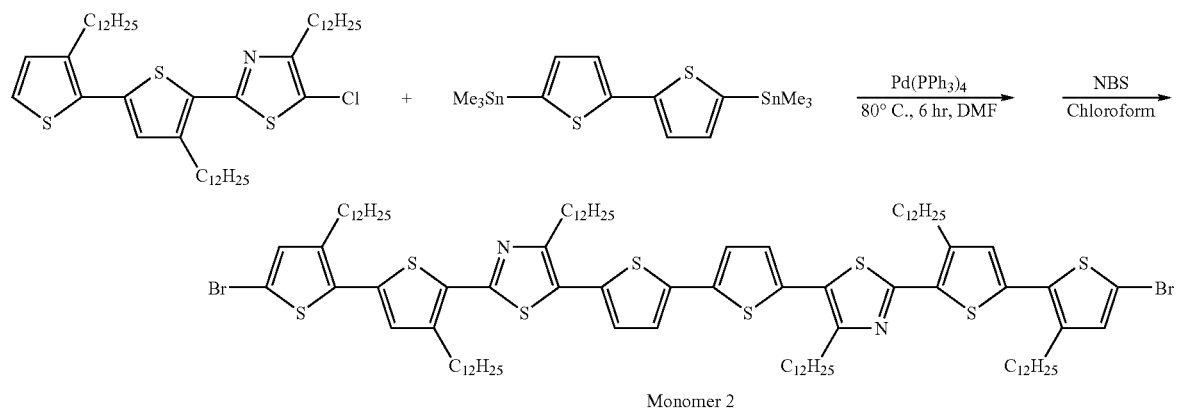

Monomer 2

The thiophene-thiazole derivative (compound 8) (about 9.5 g, about 12 mmol) prepared in Preparation Example 3 and the same amount of bis(trimethylstenyl)bithiophene were added to a reactor under nitrogen atmosphere and completely dissolved in anhydrous DMF with gentle heating. After palladium(0) compound $Pd(PPh_3)_4$ as a catalyst (about 10 mol % based on the total amount of monomers) was added thereto, the mixture was reacted at about 8° C. for about 6 hours. After the reaction was completed, the reaction solution was treated with a diluted hydrochloric acid solution and extracted with chloroform. After the organic layer thus obtained was removed by distillation under reduced vacuum, the resulting product was gently washed with methanol and dried, to obtain an organic compound containing thiazole rings. The organic compound containing thiazole rings was then reacted with NBS(N-bromosuccinimide) in a chloroform solution, to thereby obtain an organic compound containing thiazole rings (monomer-2) (about 10.1 g, yield: about 46%). The $^1$H NMR result of the monomer-2 is as follows.

acid solution/chloroform twice, ammonia solution/chloroform twice, and water/chloroform twice in sequence. The washed polymer solid was re-precipitated in methanol and dried, to thereby obtain a red polymer containing thizaole rings, Poly-4 of Formula 8 (about 0.38 g, yield: about 35%, number average molecular weight=about 25,000). The $^1$H NMR result of Poly-4 is as follows.

$^1$H NMR (300 MHz, CDCl$_3$) δ 0.87 (18H), 1.26 (108H), 1.71 (8H), 1.73 (4H), 2.80 (4H), 2.92 (8H), 6.99 (4H), 7.06 (4H), 7.16 (2H).

δ 0.86 (18H), 1.26 (108H), 1.71 (8H), 1.84 (4H), 2.80 (4H), 2.93 (8H), 6.99 (4H), 7.07 (4H), 7.16 (4H).

Preparation Example 6

Synthesis of an Organic Semiconductor Polymer Containing Thiazole Rings(Poly-5) Using Reaction Scheme 1

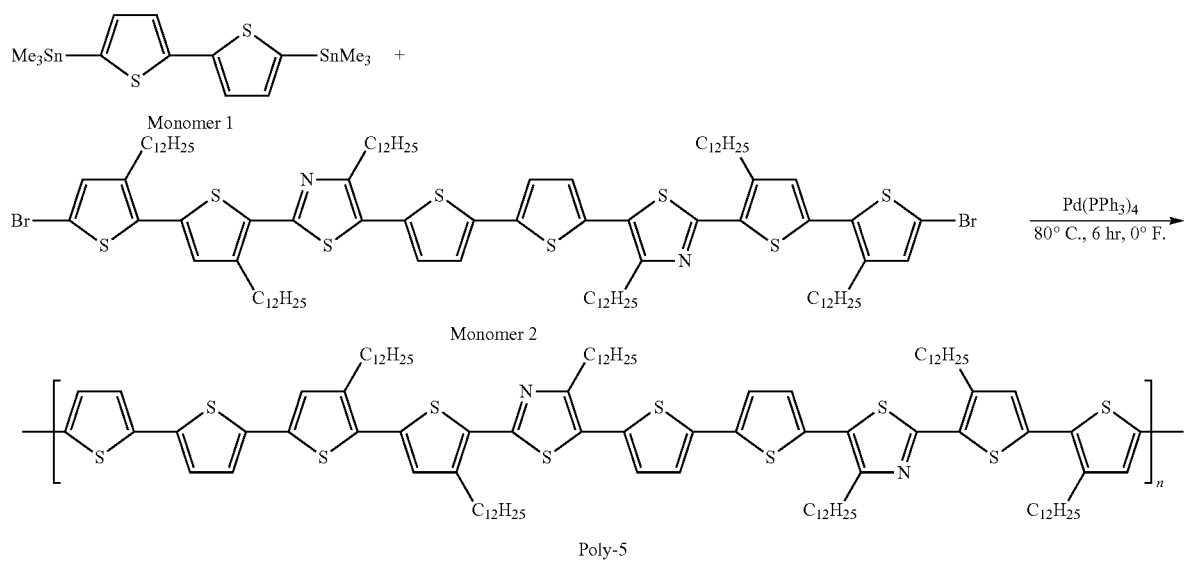

$^1$H NMR (300 MHz, CDCl$_3$) δ 0.87 (t, 18H), 1.25 (m, 108H), 1.70 (m, 12H), 2.75 (t, 4H), 2.92 (m, 8H), 6.90 (s, 4H), 7.07 (d, 2H), 7.16 (d, 2H).

Preparation Example 5

Synthesis of an Organic Semiconductor Polymer Containing Thiazole Rings(Poly-4) Using Reaction Scheme 1

The organic compound containing thiazole rings (monomer-2)(about 0.28 g, about 0.61 mmol) prepared in Preparation Example 4 and the same amount of bis(trimethylstenyl) bithiophene were added to a reactor under nitrogen atmosphere and completely dissolved in anhydrous DMF with gentle heating. After palladium(0) compound $Pd(PPh_3)_4$ as a catalyst (about 10 mol % based on the total amount of monomers) was added thereto, the mixture was reacted at about 85° C. for 5 to 6 hours. After the reaction was completed, the reaction solution was cooled to about room temperature and filtered, to obtain a polymer solid. The polymer solid so obtained was successively washed with hydrochloric A dark red organic semiconductor polymer containing thiazole rings, Poly-5 of Formula 8 (about 0.32 g, yield: about 29%, number average molecular weight=about 18,000) was synthesized according to the same method as in Preparation Example 5 except that the organic compound containing thiazole rings (monomer-2) (about 0.28 g, about 0.61 mmol) prepared in Preparation Example 4 and bis(trimethylstenyl) bithiophene (about 0.31 g, about 0.61 mmol) were used as a monomer. The $^1$H NMR result of Poly-5 is as follows.

$^1$H NMR (300 MHz, CDCl$_3$) δ 0.86 (18H), 1.26 (108H), 1.71 (8H), 1.84 (4H), 2.80 (4H), 2.93 (8H), 6.99 (4H), 7.07 (4H) 7.16 (4H).

Example 1

Manufacture of an OTFT Using Poly-4

A gate electrode was first deposited on a washed glass substrate in a thickness of about 100 Å by using chrome according to a sputtering method, and a gate insulating layer was then deposited thereon in a thickness of about 1000 Å by using SiO$_2$ according to a chemical vapor deposition (CVD)

method. A source-drain electrode was deposited on the gate insulating layer in a thickness of about 1200 Å by using ITO according to a sputtering method. The substrate was washed with isopropyl alcohol for about 10 minutes and dried before the deposition of organic semiconductor materials. The substrate was soaked in an octadecyl trichlorosilane solution diluted with chloroform into a concentration of about 10 mM for about 30 seconds, washed with acetone and dried. After the polymer containing thiazole rings, Poly-4 synthesized in Preparation Example 5 was dissolved in chloroform at a concentration of about 1 wt %, the resulting solution was coated on the substrate in a thickness of about 1000 Å at a rate of about 1000 rpm, and then, the substrate was baked at about 100° C. for about 1 hour under argon atmosphere, to thereby manufacture an OTFT device.

Example 2

Manufacture of an OTFT Using Poly-5

In this example, an OTFT device was manufactured according to the same method as described in Example 1 except that the polymer containing thiazole rings, Poly-5 synthesized in Preparation Example 6 was employed.

Comparative Example

Manufacture of an OTFT Using Poly(3-hexylthiophene)(P3HT)

An OTFT device was manufactured according to the same method as described in Example 1 except that poly hexylthiophene(P3HT, Aldrich), which does not contain oligothiophene and an n-type aromatic compound, is composed of only thiophene and has a head-to-tail structure, was employed.

Figure 3:
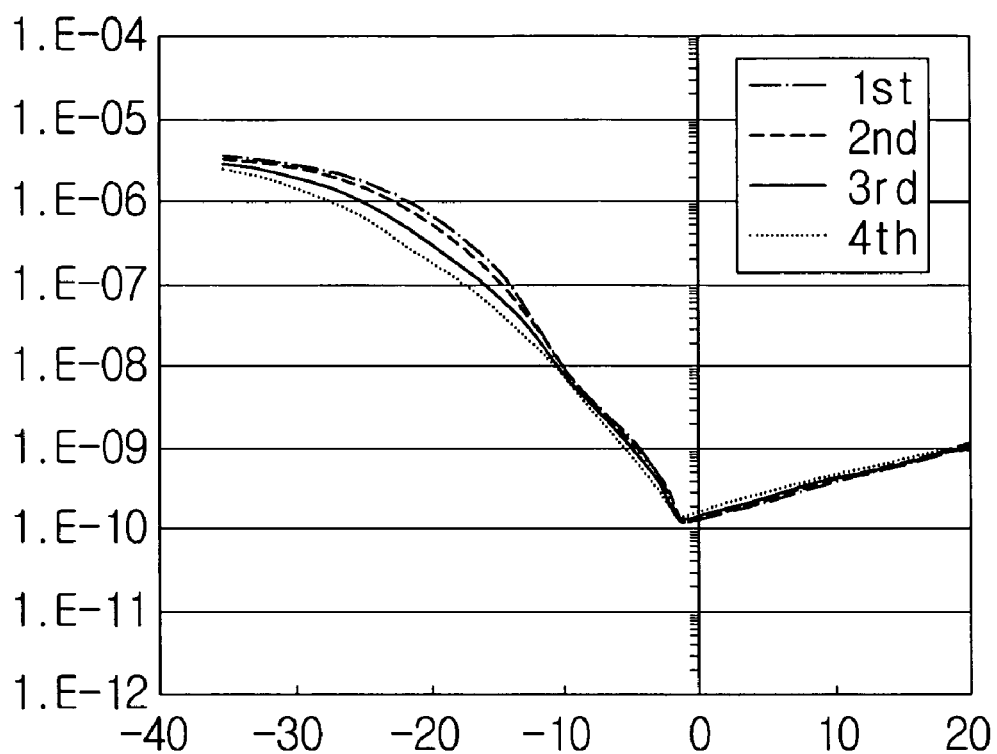
Figure 4:
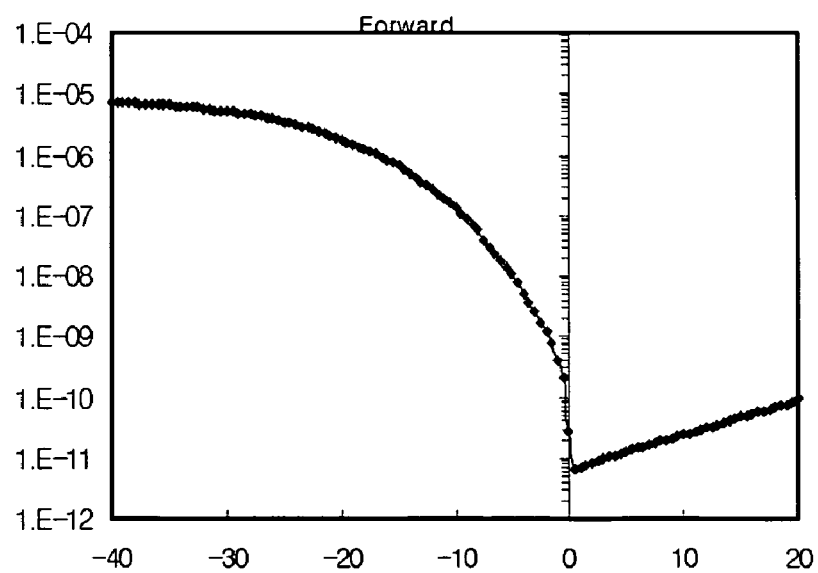
FIG. 4 is a current-transfer characteristic curve of an organic semiconductor polymer containing thiazole rings (Poly-5) prepared in Preparation Example 6 of example embodiments.

Current transfer characteristic curves of the devices prepared in Example 1, Example 2 and Comparative Example were measured by using a semiconductor characterization system 4200-SCS (KEITHLEY Instruments Inc.)(four times for Example 1, and once for Example 2), and the results are shown in FIGS. 3 and 4, respectively. Further, electrical properties determined according to the current transfer characteristic curves are shown in Table 1.

TABLE 1

| Organic active layer | Charge carrier mobility(cm²/Vs) | Current on/off ratio | Blocking leakage current(A) |
|---|---|---|---|
| Example 1 | 0.23 | $3 \times 10^4$ | $1 \times 10^{-10}$ |
| Example 2 | 0.45 | $9 \times 10^5$ | $6 \times 10^{-12}$ |
| Comparative Example | 0.045 | 1000 | $1 \times 10^{-9}$ |

The charge carrier mobility was determined from a graph that takes $(I_{SD})^{1/2}$ and $V_G$ as parameters from the following saturation region current formula:

$$I_{SD} = \frac{WC_0}{2L}\mu(V_G - V_T)^2$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

wherein $I_{SD}$ is a source-drain current, $\mu$ or $\mu_{FET}$ is charge carrier mobility; $C_0$ is oxide capacitance, W is a channel width, L is a channel length, $V_G$ is gate voltage, and $V_T$ is a threshold voltage.

The blocking leakage current ($I_{off}$) is a current flowing under a turn-off condition, and was calculated from a current ratio as a minimum current at the turn-off condition.

The current on/off ratio ($I_{on}/I_{off}$) was calculated as a ratio of a maximum current at a turn-on condition and a minimum current at the turn-off condition.

As may be seen from Table 1, the organic semiconductor polymers containing thiazole rings prepared in Examples 1 and 2 showed reduced leakage current at the turn-off condition of OTFT and increased current on/off ratio and charge carrier mobility, as compared with polyhexylthiophene of the Comparative Example.

As apparent from the foregoing, the organic semiconductor polymers according to example embodiments may contain hetero arylene or arylene showing a p-type semiconductor property in addition to thiophene showing a p-type semiconductor property and thiazole rings showing a n-type semiconductor property at a polymer main chain, thus exhibiting increased solubility to a general organic solvent, coplanarity, processibility and an improved thin film property. Further, when the organic semiconductor polymers of example embodiments are applied to an organic channel layer of an OTFT, the OTFT may acquire increased charge carrier mobility and decreased blocking leakage current.

Although example embodiments have been disclosed for illustrative purposes, those skilled in the art will appreciate that various modifications, additions and substitutions are possible, without departing from the scope and spirit of the accompanying claims.

What is claimed is:

1. A compound represented by the following Formula 1:

[Formula 1]

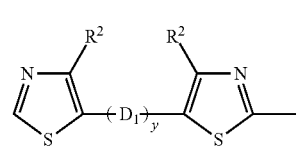

wherein $R^2$ is hydrogen, hydroxy, linear, branched or cyclic $C_{1\sim20}$ alkyl, $C_{1\sim20}$ alkoxyalkyl, or linear, branched or cyclic $C_{1\sim16}$ alkoxy; $D_1$ is $C_{2\sim20}$ hetero arylene or $C_{6\sim30}$ arylene; and y is an integer ranging from 1 to 4.

2. The compound of claim 1, wherein the hetero arylene is a 5-membered hetero arylene substituted with one or more elements selected from the group consisting of S, N—H, O and Se.

3. The compound of claim 1, wherein the hetero arylene and arylene are substituted with one or more elements selected from the group consisting of hydroxy, linear, branched or cyclic $C_1\sim C_{20}$ alkyl, $C_1\sim C_{20}$ alkoxyalkyl, linear, branched or cyclic $C_1\sim C_{16}$ alkoxy, F, Br, Cl and I.

4. The compound of claim 1, wherein the hetero arylene and arylene are selected from the compounds represented by the following Formula 2:
[Formula 2]
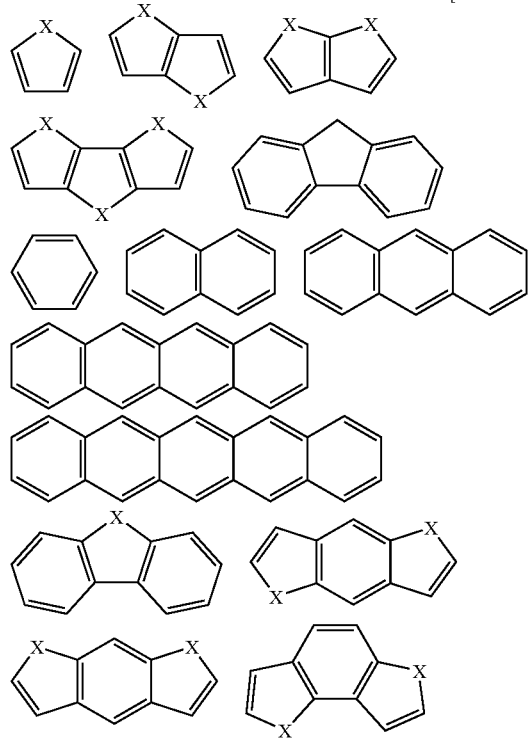
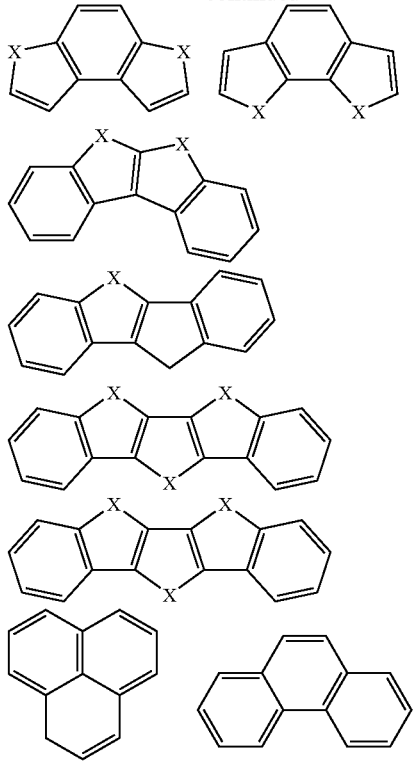
wherein X is S, N—H, O or Se.
* * * * *